United States Patent
Onishi et al.

(10) Patent No.: US 8,398,340 B2
(45) Date of Patent: Mar. 19, 2013

(54) METHOD OF EXTRACTING CONTENTS FROM THE INSIDE OF A REACTOR KEPT AT HIGH TEMPERATURE AND HIGH PRESSURE, AND SYNTHESIS REACTION SYSTEM OF HYDROCARBON COMPOUND

(75) Inventors: Yasuhiro Onishi, Tokyo (JP); Yuzuru Kato, Tokyo (JP); Atsushi Murata, Tokyo (JP); Eiichi Yamada, Tokyo (JP)

(73) Assignees: Nippon Steel Engineering Co., Ltd., Tokyo (JP); Japan Oil, Gas and Metals National Corporation, Kanagawa (JP); Inpex Corporation, Tokyo (JP); JX Nippon Oil & Energy Corporation, Tokyo (JP); Japan Petroleum Exploration Co., Ltd., Tokyo (JP); Cosmo Oil Co., Ltd., Tokyo (JP)

( * ) Notice: Subject to any disclaimer, the term of this patent is extended or adjusted under 35 U.S.C. 154(b) by 319 days.

(21) Appl. No.: 12/736,114

(22) PCT Filed: Mar. 12, 2009

(86) PCT No.: PCT/JP2009/054788
§ 371 (c)(1),
(2), (4) Date: Nov. 5, 2010

(87) PCT Pub. No.: WO2009/113625
PCT Pub. Date: Sep. 17, 2009

(65) Prior Publication Data
US 2011/0039957 A1    Feb. 17, 2011

(30) Foreign Application Priority Data
Mar. 14, 2008  (JP) ................................ 2008-066155

(51) Int. Cl.
*B65G 53/12*  (2006.01)
*B01J 10/00*  (2006.01)

(52) U.S. Cl. ........ 406/146; 406/195; 422/187; 422/132; 422/140; 514/718; 208/400

(58) Field of Classification Search ........................ None
See application file for complete search history.

(56) References Cited

U.S. PATENT DOCUMENTS
4,260,298 A    4/1981  Zenz
2006/0272986 A1    12/2006  Steynberg

FOREIGN PATENT DOCUMENTS
JP    56-2839    1/1981
JP    2001-318033    11/2001

OTHER PUBLICATIONS
JP2001-318033, Tokyo Gas Co Ltd, Device for sampling solid particles, Nov. 16, 2001, English Translation, 11 pages.*
International Search Report dated Jun. 16, 2009 issued in corresponding PCT Application No. PCT/JP2009/054788.
The Japan Petroleum Institute Shin Energy Bukai Koenkai, Jul. 6, 2007.

\* cited by examiner

*Primary Examiner* — Yate K Cutliff
(74) *Attorney, Agent, or Firm* — Kenyon & Kenyon LLP

(57) ABSTRACT

A method of extracting the contents from the inside of a reactor kept at high temperature and high pressure includes the steps of introducing the contents of the reactor into a pipe having an internal space which communicates with the reactor, closing the pipe to enclose the contents in the internal space, removing unnecessary gas from the internal space, and supplying an inert gas to the internal space, thereby replacing the contents enclosed in the internal space with the inert gas. The contents are discharged from the internal space by replacing the contents enclosed in the internal space with the inert gas.

9 Claims, 4 Drawing Sheets

US 8,398,340 B2

METHOD OF EXTRACTING CONTENTS FROM THE INSIDE OF A REACTOR KEPT AT HIGH TEMPERATURE AND HIGH PRESSURE, AND SYNTHESIS REACTION SYSTEM OF HYDROCARBON COMPOUND

TECHNICAL FIELD

The present invention relates to a method of extracting contents from the inside of a reactor (for example, a synthesis reactor of a hydrocarbon compound) kept at high temperature and high pressure, in a synthesis reaction system of a hydrocarbon compound for synthesizing the hydrocarbon compound by introducing a synthesis gas including carbon monoxide gas and hydrogen gas as main components into a slurry having solid catalyst particles suspended in liquid hydrocarbons, and a synthesis reaction system of a hydrocarbon compound.

This application is a national stage application of International Application No. PCT/JP2009/054788, filed 12 Mar. 2009, which claims priority to Japanese Patent Application No. 2008-66155, filed Mar. 14, 2008, the content of which is incorporated herein by reference.

BACKGROUND ART

As synthesis reaction systems of a hydrocarbon compound which synthesize hydrocarbon compounds by a Fischer-Tropsch synthesis reaction (hereinafter referred to as "FT synthesis reaction") by using a synthesis gas mainly composed of carbon monoxide gas (CO) and hydrogen gas ($H_2$) as a raw material gas, for example, like the PATENT DOCUMENT 1, there is a bubble column type slurry bed FT reaction system which carries out the FT synthesis reaction by introducing the synthesis gas into a slurry in which solid catalyst particles are suspended in liquid hydrocarbons. A hydrocarbon compound synthesized by the FT synthesis reaction is mainly utilized as a raw material for liquid fuel products such as naphtha (raw gasoline), kerosene, and gas oil.

In an FT synthesis reactor provided for the conventional bubble column type slurry bed FT reaction system as described above, in order to investigate the carbon number distribution of a hydrocarbon compound synthesized inside the reactor, reaction state generated by a reaction between the slurry and a source gas, and the concentration distribution of the slurry inside the reactor, it is necessary to extract contents, in which the slurry and the source gas are mixed, from the synthesis reactor.

PATENT DOCUMENT 1: Specification of US Patent Application Publication No. 2006-0272986

DISCLOSURE OF THE INVENTION

Problem that the Invention is to Solve

However, since the inside of the reactor is kept at high temperature and high pressure, and inflammable gases or toxic gases are included in the contents to be extracted, it is difficult to safely and accurately extract the contents, in which the slurry and the synthesis gas are mixed, from the synthesis reactor.

The present invention has been made in view of such problems, and aims at providing a method of safely and accurately extracting contents from the inside of a reactor kept at high temperature and high pressure, in a synthesis reaction system of a hydrocarbon compound which synthesizes a hydrocarbon compound by an FT synthesis reaction, and a synthesis reaction system of a hydrocarbon compound.

Means for Solving the Problem

The method of extracting the contents of the present invention is a method of extracting the contents from the inside of a reactor kept at high temperature and high pressure. The method includes the steps of introducing the contents of the reactor into a pipe having an internal space which communicates with the reactor, closing the pipe to enclose the contents in the internal space, removing unnecessary gas from the internal space, and supplying an inert gas to the internal space, thereby replacing the contents enclosed in the internal space with the inert gas. The contents are discharged from the internal space by replacing the contents enclosed in the internal space with the inert gas.

In the method of extracting the contents of the present invention, the reactor may be a synthesis reactor which synthesizes a hydrocarbon compound by a chemical reaction between a synthesis gas including hydrogen and carbon monoxide as main components and a slurry having solid catalyst particles suspended in liquid.

According to the method of extracting the contents of the present invention, unnecessary gas is removed from the space after the contents are introduced into the space from the inside of the reactor (for example, FT synthesis reactor) kept at high temperature and high pressure and the space is closed. Thereby, gas (for example, an inflammable gas or a toxic gas) included in the contents can be safely removed from the contents dispensed into the space. Then, the contents are discharged from the space by supplying an inert gas to the space and replacing the contents within the space with the inert gas. Thereby, the contents can be safely discharged from the reactor kept at high temperature and high pressure.

A synthesis reaction system of a hydrocarbon compound of the present invention includes a synthesis reactor which synthesizes a hydrocarbon compound by a chemical reaction between a synthesis gas including hydrogen and carbon monoxide as main components and a slurry having solid catalyst particles suspended in liquid, an extracting devices which extracts the contents, in which the synthesis gas and the slurry are mixed, from the synthesis reactor, and a storage tank which stores the remaining components of the contents extracted from the synthesis reactor. The extracting devices includes a main pipe interposed between the synthesis reactor and the storage tank, having an internal space communicating with the synthesis reactor, and allowing the contents introduced from the synthesis reactor to be enclosed in the internal space, an inert gas supply section supplying an inert gas to the internal space, a gas vent pipe allowing unnecessary gas to be removed from the internal space of the main pipe on the downstream side of a connection point with the inert gas supply section, an extraction pipe allowing the contents of the reactor enclosed in the internal space to be discharged to an extraction vessel from the main pipe on the downstream side of a connection point with the gas vent pipe, and a three-way valve provided at a connection point between the main pipe and the extraction pipe to switch a discharge direction of the contents enclosed in the internal space to either the storage tank or the extraction vessel.

According to the synthesis reaction system of a hydrocarbon compound of the present invention, unnecessary gas is removed to the outside of the system through the gas vent pipe from the space after the contents are introduced into the internal space of the main pipe from the inside of the synthesis reactor kept at high temperature and high pressure, and the internal space is closed. Thereby, an inflammable gas or a toxic gas included in the contents can be safely removed from the contents held in the internal space of the main pipe. Thereafter, when the three-way valve is switched to the storage tank, an inert gas is supplied to the main pipe from the inert gas supply section, the contents within this space are replaced with the inert gas and are extracted from the main pipe to the extraction vessel through the extraction pipe. Thereby, the contents can be safely extracted from the synthesis reactor kept at high temperature and high pressure.

In the synthesis reaction system of a hydrocarbon compound of the present invention, a plurality of the extracting devices may be installed in the synthesis reactor so as to be spaced apart in a vertical direction of the reactor or may be installed in the synthesis reactor so as to be spaced apart in a peripheral direction of the reactor.

If a plurality of extracting devices are installed so as to be spaced apart in the vertical direction of the synthesis reactor, it is possible to investigate the carbon number distribution of a product (a hydrocarbon compound) included in the contents in the vertical direction within the synthesis reactor, the distribution of reaction state in the vertical direction within the synthesis reactor, and the concentration distribution of the slurry in the vertical direction within the synthesis reactor.

If a plurality of extracting devices are installed so as to be spaced apart in the peripheral direction of the synthesis reactor, it is possible to investigate the carbon number distribution of a product included in the contents in the peripheral direction within the synthesis reactor, the distribution of the reaction state in the peripheral direction within the synthesis reactor, and the concentration distribution of the slurry in the peripheral direction within the synthesis reactor.

In the synthesis reaction system of a hydrocarbon compound according to the present invention, the main pipe may be provided with a quantitative section which obtains a predetermined quantity of the contents.

Further, since a predetermined quantity of the contents obtained by the quantitative section provided in the main pipe is extracted to the extraction vessel, a required quantity of the contents can be extracted to the extraction vessel.

In the synthesis reaction system of a hydrocarbon compound of the present invention, the quantitative section may be formed in the shape of a pipe of which the capacity of the internal space is almost equal to the predetermined quantity, and may be installed so as to incline at a predetermined angle to a horizontal plane. By installing the quantitative section inclinedly, a predetermined quantity of the contents obtained by the quantitative section is smoothly discharged from the quantitative section by the action of gravity on itself.

Preferably, the size of the predetermined angle is equal to or more than the angle of repose of the catalyst particles included in such contents, for example, equal to or more than 45 degrees. The angle of repose is an angle at which the contents keep their stability spontaneously. By making the quantitative section incline more largely than the angle of repose, the contents can be made to flow into the extraction vessel smoothly from the quantitative section.

In the synthesis reaction system of a hydrocarbon compound of the present invention, an upper face of the quantitative section may be formed in a planar shape. By forming an upper face of the quantitative section in a planar shape, gas included in the contents within the quantitative section can be vented easily.

Advantage of the Invention

According to the present invention, the contents in which a slurry and a synthesis gas are mixed can be safely and accurately extracted from the synthesis reactor. Further, it is possible to investigate the carbon number distribution of a product (i.e., a hydrocarbon compound) included in the contents within the synthesis reactor, the distribution of reaction state within the synthesis reactor, and the concentration distribution of the slurry within the synthesis reactor.

DESCRIPTION OF REFERENCE NUMERALS

1: LIQUID FUEL SYNTHESIZING SYSTEM (SYNTHESIS REACTION SYSTEM OF HYDROCARBON COMPOUNDS)
30: BUBBLE COLUMN REACTOR(SYNTHESIS REACTOR)
42: EXTRACTING DEVICE
43: EXTRACTION VESSEL
44: STORAGE TANK
45: MAIN PIPE
46: INERT GAS SUPPLY PIPE
47: GAS VENT PIPE
48: EXTRACTION PIPE
49: THREE-WAY VALVE
90: QUANTITATIVE SECTION
θ: INCLINATION ANGLE

BEST MODE FOR CARRYING OUT THE INVENTION

Hereinafter, a first embodiment of the present invention will be described with reference to FIGS. 1 to 4.

Figure 1:
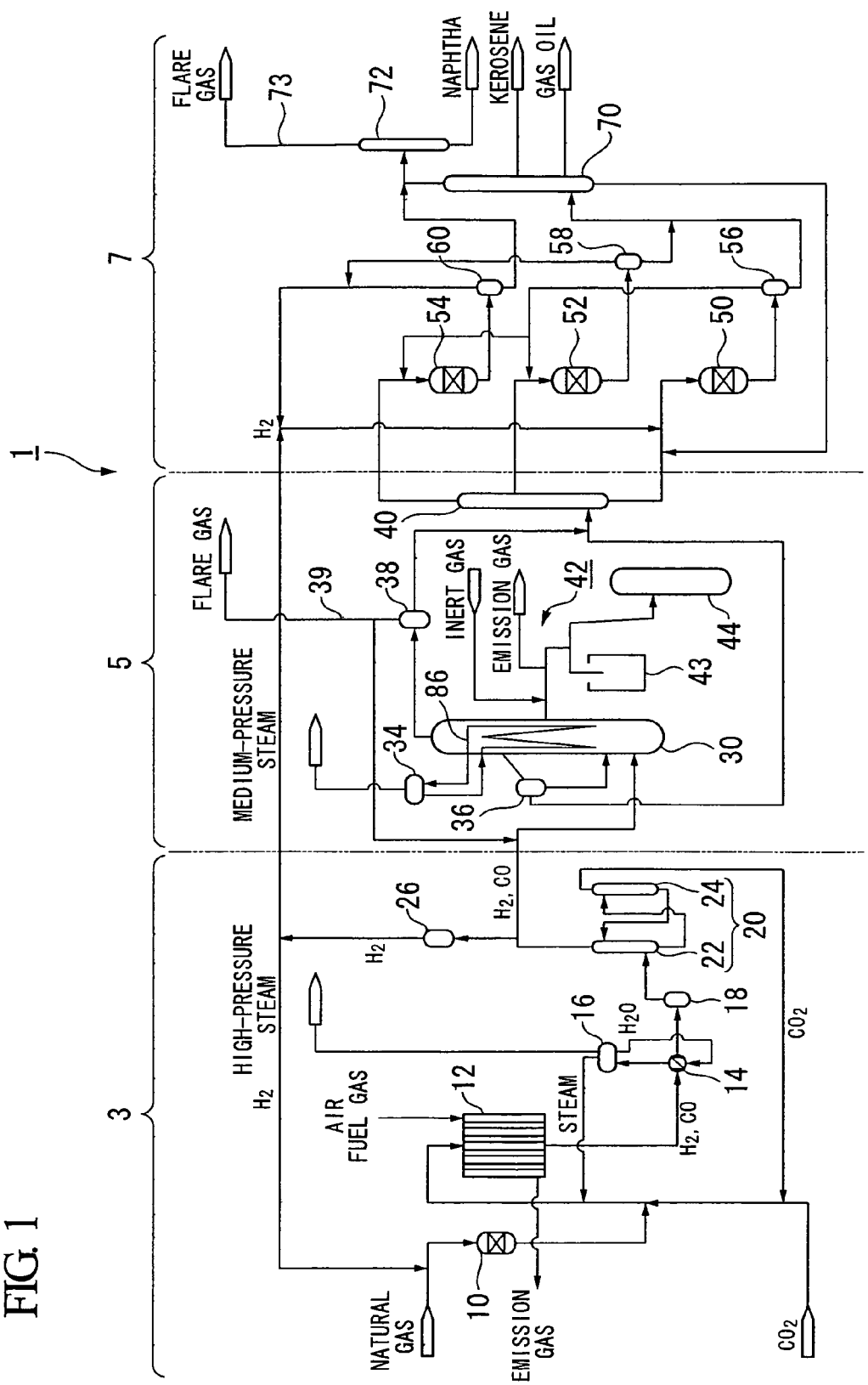
FIG. 1 is a schematic diagram showing the overall configuration of a liquid fuel synthesizing system according to a first embodiment of the invention.

As shown in FIG. 1, the liquid fuel synthesizing system (synthesis reaction system of hydrocarbon compounds) 1 according to the present embodiment is a plant facility which carries out the GTL process which converts a hydrocarbon raw material, such as natural gas, into liquid fuel. This liquid fuel synthesizing system 1 includes a synthesis gas production unit 3, an FT synthesis unit 5, and an upgrading unit 7. The synthesis gas production unit 3 reforms natural gas, which is a hydrocarbon raw material, to produce synthesis gas including carbon monoxide gas and hydrogen gas. The FT synthesis unit 5 produces liquid hydrocarbons from the produced synthesis gas by the Fischer-Tropsch synthesis reaction (hereafter referred to as "FT synthesis reaction"). The upgrading unit 7 hydrogenates and hydrocracks the liquid hydrocarbons produced by the FT synthesis reaction to obtain liquid fuel products (naphtha, kerosene, gas oil, wax, etc.). Hereinafter, constituent parts of each of these units will be described.

The synthesis gas production unit 3 mainly includes, for example, a desulfurizing reactor 10, a reformer 12, a waste heat boiler 14, gas-liquid separators 16 and 18, a $CO_2$ removal unit 20, and a hydrogen separating apparatus 26. The desulfurizing reactor 10 is composed of a hydrodesulfurizer, etc., and removes sulfur components from natural gas as a raw material. The reformer 12 reforms the natural gas supplied from the desulfurizing reactor 10, to produce synthesis gas including carbon monoxide gas (CO) and hydrogen gas ($H_2$) as main components. The waste heat boiler 14 recovers waste heat of the synthesis gas produced by the reformer 12, to produce high-pressure steam. The gas-liquid separator 16 separates the water heated by heat exchange with the synthesis gas in the waste heat boiler 14 into vapor (high-pressure steam) and liquid. The gas-liquid separator 18 removes condensate from the synthesis gas cooled down in the waste heat boiler 14, and supplies a gas component to the $CO_2$ removal unit 20. The $CO_2$ removal unit 20 has an absorption column 22 which removes carbon dioxide gas by using an absorbent from the synthesis gas supplied from the gas-liquid separator 18, and a regeneration column 24 which desorbs the carbon dioxide gas and regenerates the absorbent including the carbon dioxide gas. The hydrogen separating apparatus 26 separates a portion of the hydrogen gas included in the synthesis gas, the carbon dioxide gas of which has been separated by the $CO_2$ removal unit 20. It is to be noted herein that the above $CO_2$ removal unit 20 need not be provided depending on circumstances.

Among them, the reformer 12 reforms natural gas by using carbon dioxide and steam to produce high-temperature synthesis gas including carbon monoxide gas and hydrogen gas as main components, by a steam and carbon-dioxide-gas reforming method expressed by the following chemical reaction formulas (1) and (2). In addition, the reforming method in this reformer 12 is not limited to the example of the above steam and carbon-dioxide-gas reforming method. For example, a steam reforming method, a partial oxidation reforming method (POX) using oxygen, an autothermal reforming method (ATR) that is a combination of the partial oxidation method and the steam reforming method, a carbon-dioxide-gas reforming method, and the like can also be utilized.

$$CH_4 + H_2O \rightarrow CO + 3H_2 \quad (1)$$

$$CH_4 + CO_2 \rightarrow 2CO + 2H_2 \quad (2)$$

Further, the hydrogen separating apparatus 26 is provided on a line branched from a main pipe which connects the $CO_2$ removal unit 20 or gas-liquid separator 18 with the bubble column reactor 30. This hydrogen separating apparatus 26 can be composed of, for example, a hydrogen PSA (Pressure Swing Adsorption) device which performs adsorption and desorption of hydrogen by using a pressure difference. This hydrogen PSA device has adsorbents (zeolitic adsorbent, activated carbon, alumina, silica gel, etc.) within a plurality of adsorption columns (not shown) which are arranged in parallel. By sequentially repeating processes including pressurizing, adsorption, desorption (pressure reduction), and purging of hydrogen in each of the adsorption columns, high-purity (for example, about 99.999%) hydrogen gas separated from the synthesis gas can be continuously supplied to various hydrogen-utilizing reaction devices (for example, the desulfurizing reactor 10, the WAX fraction hydrocracking reactor 50, the kerosene and gas oil fraction hydrotreating reactor 52, the naphtha fraction hydrotreating reactor 54, etc.) which perform predetermined reactions.

In addition, the hydrogen gas separating method in the hydrogen separating apparatus 26 is not limited to the example of the pressure swing adsorption method as in the above hydrogen PSA device. For example, there may be a hydrogen storing alloy adsorption method, a membrane separation method, or a combination thereof.

Figure 2:
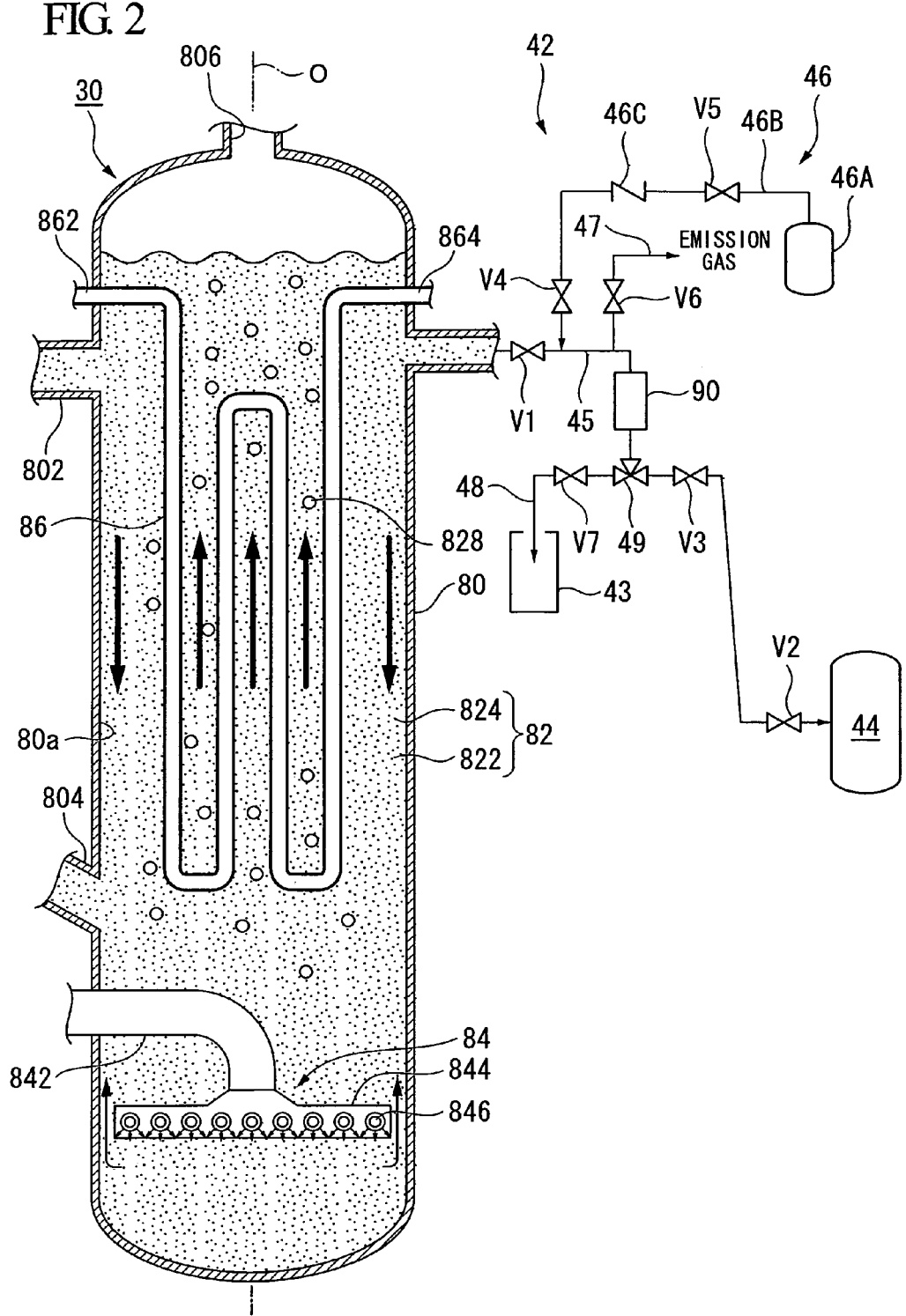
FIG. 2 is a schematic view showing a reactor constituting the liquid fuel synthesizing system of FIG. 1, and an extracting device installed in the reactor.

Next, the FT synthesis unit 5 will be described. The FT synthesis unit 5 mainly includes, for example, the bubble column reactor (synthesis reactor) 30, a gas-liquid separator 34, a separator 36, a gas-liquid separator 38, a first fractionator 40, an extracting device 42, and a storage tank 44. The bubble column reactor 30, which is an example of a reactor which converts synthesis gas into liquid hydrocarbons, functions as an FT synthesis reactor which synthesizes liquid hydrocarbons from synthesis gas by the FT synthesis reaction. The bubble column reactor 30, as shown in FIG. 2, mainly includes a reactor main body 80, a distributor 84 and a cooling pipe 86.

The reactor main body 80 is a substantially cylindrical vessel made of metal, the diameter of which is about 1 to 20 meters, preferably about 2 to 10 meters. The height of the reactor main body 80 is about 10 to 50 meters, preferably about 15 to 45 meters. Slurry 82 having solid catalyst particles 824 suspended in liquid hydrocarbons (product of the FT synthesis reaction) 822 is accommodated inside the reactor main body 80. The reactor main body 80 is formed with a slurry outflow port 802 through which a portion of the slurry 82 is allowed to flow out to the separator 36 from an upper portion of the reactor main body, and a slurry inflow port 804 through which the slurry 82 including a number of catalyst particles 824 is allowed to flow into a lower portion of the reactor main body 80 from the separator 36, and an unreacted gas outlet 806 which supplies unreacted synthesis gas, etc. to the gas-liquid separator 38 from the top of the reactor main body 80.

The distributor 84, which is an example of a synthesis gas supplying section according to the present embodiment, is disposed at the lower portion inside the reactor main body 80 to supply synthesis gas including hydrogen and carbon monoxide as main components into the slurry 82. The distributor 84 is composed of a synthesis gas supply pipe 842, a nozzle header 844 attached to a distal end of the synthesis gas supply pipe 842, and a plurality of synthesis gas supply nozzles 846 provided at a side portion of the nozzle header 844.

The synthesis gas supplied through the synthesis gas supply pipe 842 from the outside of the reactor passes through the nozzle header 844 and is introduced into the slurry 82 inside the reactor main body 80 from a synthesis gas supply port (not shown) provided at a lower portion of each of synthesis gas supply nozzles 846 (at the bottom of the reactor main body 80). In addition, in the present embodiment, although the synthesis gas is injected toward the lower portion (direction shown by the thin arrows in the drawing) of the reactor main body 80, the synthesis gas may be injected toward the upper portion of the reactor main body 80.

Thus, the synthesis gas injected into the slurry 82 from the distributor 84 is made into bubbles 828, and flows through the slurry 82 from the bottom toward the top in the vertical direction of the reactor main body 80. In the process, the synthesis gas is dissolved in the liquid hydrocarbons 822 and brought into contact with the catalyst particles 824, whereby a synthesis reaction of the liquid hydrocarbons (FT synthesis reaction) is carried out. Specifically, as shown in the following chemical reaction formula (3), the hydrogen gas and the carbon monoxide gas follow a synthesis reaction.

$$2nH_2 + nCO \rightarrow (CH_2)_n + nH_2O \quad (3) \text{ (where } n \text{ is a positive integer)}$$

Further, the synthesis gas is introduced into the slurry 82 from the distributor 84 disposed at the lower portion inside the reactor main body 80. The synthesis gas introduced into the slurry is made into bubbles 828 and ascends through the reactor main body 80. Thereby, inside the reactor main body 80, an upward flow (air lift) of the slurry 82 is generated at the central portion inside the reactor main body 80 and in the vicinity thereof (that is, in the vicinity of the center axis of the reactor main body 80), and a downward flow of the slurry 82 is generated in the vicinity of the inner wall of the reactor main body 80 (that is, in the vicinity of the inner peripheral portion). Thereby, as shown by the thick arrows in FIG. 2, a circulating flow of the slurry 82 is generated inside the reactor main body 80.

The cooling pipe 86 is provided along the vertical direction of the reactor main body 80 inside the reactor main body 80 to cool down the slurry 82, the temperature of which has risen due to the heat generated by the FT synthesis reaction. The cooling pipe 86 may be formed so as to reciprocate a plurality of times (for example, reciprocate twice in FIG. 2) in the vertical direction, for example, by bending a single pipe as shown in FIG. 2. However, the shape and number of cooling pipes are not limited to the above shape and number, but may be such that the cooling pipes are evenly arranged inside the reactor main body 80 and contribute to uniform cooling of the slurry 82. For example, a plurality of cooling pipes having a double-pipe structure called a bayonet type may be arranged inside the reactor main body 80.

Cooling water (for example, the temperature of which is different by about −50 to 0° C. from the interior temperature of the reactor main body 80) introduced from the cooling pipe inlet 862 is circulated through the cooling pipe 86. As the cooling water exchanges heat with the slurry 82 via the wall of the cooling pipe 86 in the process during which the cooling water circulates through the cooling pipe 86, the slurry 82 inside the reactor main body 80 is cooled down. A portion of the cooling water, as shown in FIG. 1, can be discharged to the gas-liquid separator 34 from the cooling pipe outlet 864 as steam, and recovered as medium-pressure steam. In addition, the medium for cooling the slurry 82 is not limited to the cooling water as described above. For example, a straight chain and branched-chain paraffin, naphthene, olefin, low-molecular-weight silane, silyl ether, and silicone oil, etc., of $C_4$ to $C_{10}$ may be used as the medium.

As shown in FIGS. 1 and 2, the gas-liquid separator 34 separates the water circulated and heated through the cooling pipe 86 disposed in the bubble column reactor 30 into steam (medium-pressure steam) and liquid. The separator 36 is connected to the slurry outflow port 802 of the bubble column reactor 30, to separate the liquid hydrocarbons 822 and catalyst particles 824 of the slurry 82. Further, the separator 36 is also connected to the slurry inflow port 804 of the bubble column reactor 30, and the slurry 82 including a number of catalyst particles 824 flows into the bubble column reactor 30 from the separator 36. The gas-liquid separator 38 is connected to the unreacted gas outlet 806 of the bubble column reactor 30 to cool down unreacted synthesis gas and gaseous hydrocarbons. The first fractionator 40 distills the liquid hydrocarbons supplied via the separator 36 and the gas-liquid separator 38 from the bubble column reactor 30, and separates and refines the liquid hydrocarbons into individual fractions according to boiling points.

As shown in FIG. 2, the extracting device 42 extracts contents, in which the slurry and the synthesis gas are mixed, from the inside of the bubble column reactor 30 kept at high temperature and high pressure. The storage tank 44 stores the remnants of the contents extracted from the bubble column reactor 30. The extracting device 42 includes a main pipe 45, an inert gas supply section 46, a gas vent pipe 47, an extraction pipe 48, and a three-way valve 49. The main pipe 45 is interposed between the bubble column reactor 30 and the storage tank 44 to connect both together. The main pipe 45 is provided with a two-way valve V1 which blocks the main pipe 45 on the side of the reactor 30, a two-way valve V2 which blocks the main pipe 45 on the side of the storage tank 44, and a two-way valve V3 which blocks the main pipe 45 on the downstream side of the three-way valve 49. The inert gas supply section 46 includes an inert gas supply source 46A which supplies an inert gas, such as nitrogen gas, and an inert gas supply pipe 46B which is interposed between the main pipe 45 and the inert gas supply source 46A to connect both together. The inert gas supply pipe 46B is provided with a two-way valve V4 which blocks the inert gas supply pipe 46B on the side of the main pipe 45, a check valve 46C which prevents backward flow of the contents from the main pipe 45 to the inert gas supply source 46A, and a two-way valve V5 which blocks the inert gas supply pipe 46B on the side of the inert gas supply source 46A. The gas vent pipe 47 is connected to the main pipe 45 on the downstream side of a connection point with the inert gas supply section 46. A connection point between the main pipe 45 and the gas vent pipe 47 is arranged at a highest position in the main pipe 45. The gas vent pipe 47 is provided with a two-way valve V6 which blocks the gas vent pipe 47. The extraction pipe 48 is connected to the main pipe 45 on the downstream side of a connection point with the gas vent pipe 47. The extraction pipe 48 is provided with a two-way valve V7 which blocks the extraction pipe 48. A three-way valve 49 is provided at a connection point between the main pipe 45 and the extraction pipe 48, and switches a discharge direction of contents which have flowed into the main pipe 45 to either the storage tank 44 or an extraction vessel 43.

Figure 3:
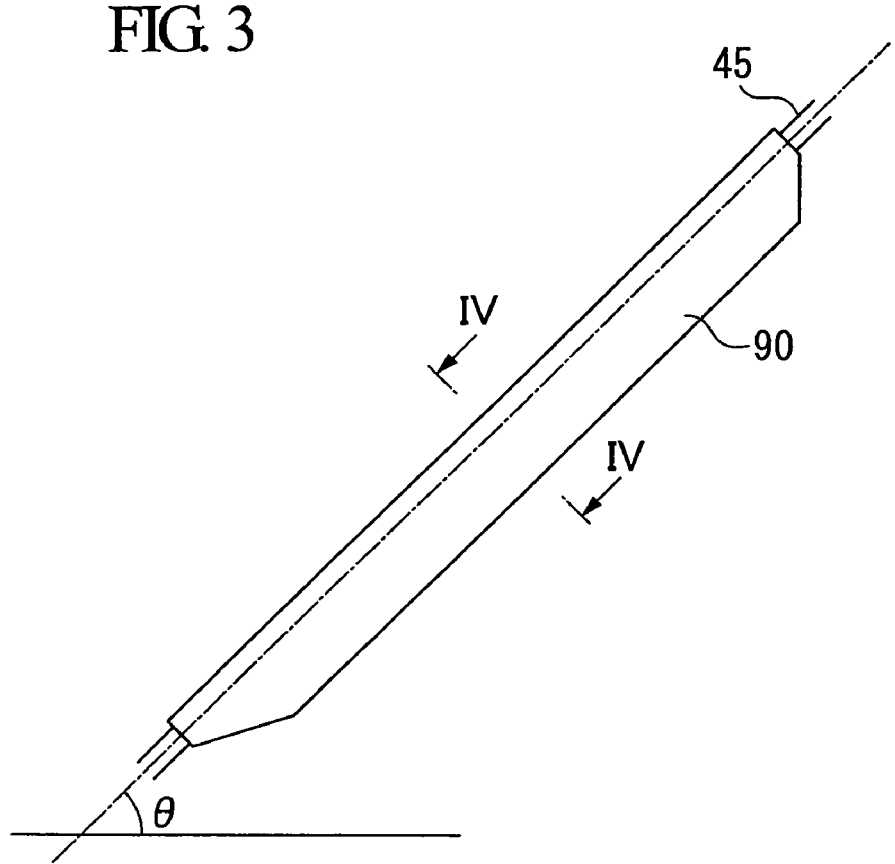
FIG. 3 is a side view showing a quantitative section constituting the extracting device of FIG. 2.
Figure 4:
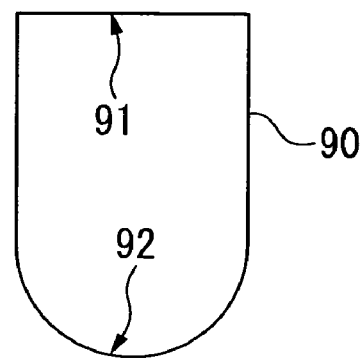
FIG. 4 is a cross-sectional view taken along line IV-IV in FIG. 3.

The main pipe 45 on the upstream side of the three-way valve 49 is provided with a quantitative section 90 for securing a predetermined quantity of contents. The quantitative section 90, as shown in FIGS. 3 and 4, is formed in the shape of a pipe of which the capacity of an internal space is almost equal to the predetermined quantity, and is installed so as to incline at a predetermined angle to a horizontal plane. Since the contents are a mixture of slurry and a source gas, it is preferable that the size of the inclination angle θ of the quantitative section 90 is equal to or more than the angle of repose of catalyst particles included in such contents, for example, equal to or more than 45 degrees). An upper face 91 inside the quantitative section 90 is formed in a planar shape from a lower end of the quantitative section 90 to an upper end thereof, and a bottom face 92 inside the quantitative section 90 informed in a circular-arc shape such that all liquid contents run down. Further, both the upper and lower ends of the quantitative section 90 are formed in a tapered shape such that a level difference is not produced with the main pipe 45.

In order to extract contents from the bubble column reactor 30 kept at high temperature and high pressure by using the extracting device 42, first, the contents are introduced into an internal space of the main pipe 45 from the inside of the bubble column reactor 30 and the internal space is closed. Thereafter, unnecessary gas is discharged out of the system through the gas vent pipe 47 from this space. Thereafter, when the three-way valve 49 is switched to the extraction vessel 43, an inert gas is supplied to the main pipe 45 from the inert gas supply section 46 and the contents within this space are replaced with the inert gas and then extracted from the main pipe 45 to the extraction vessel 43 through the extraction pipe 48 (the details thereof will be mentioned later).

Finally, the upgrading unit 7 will be described. The upgrading unit 7 includes, for example, a WAX fraction hydrocracking reactor 50, a kerosene and gas oil fraction hydrotreating reactor 52, a naphtha fraction hydrotreating reactor 54, gas-liquid separators 56, 58 and 60, a second fractionator 70, and a naphtha stabilizer 72. The WAX fraction hydrocracking reactor 50 is connected to a lower portion of the first fractionator 40. The kerosene and gas oil fraction hydrotreating reactor 52 is connected to a central portion of the first fractionator 40. The naphtha fraction hydrotreating reactor 54 is connected to an upper portion of the first fractionator 40. The gas-liquid separators 56, 58 and 60 are provided so as to correspond to the hydrogenation reactors 50, 52 and 54, respectively. The second fractionator 70 separates and refines the liquid hydrocarbons supplied from the gas-liquid separators 56 and 58 according to boiling points. The naphtha stabilizer 72 fractionates liquid hydrocarbons of a naphtha fraction supplied from the gas-liquid separator 60 and the second fractionator 70. Then, the naphtha stabilizer 72 discharges components lighter than butane toward flare gas, and separates and recovers components having a carbon number of five or more as a naphtha product.

Next, a process (GTL process) of synthesizing liquid fuel from natural gas by the liquid fuel synthesizing system 1 configured as above will be described.

Natural gas (the main component of which is $CH_4$) as a hydrocarbon raw material is supplied to the liquid fuel synthesizing system 1 from an external natural gas supply source (not shown), such as a natural gas field or a natural gas plant. The above synthesis gas production unit 3 reforms this natural gas to produce synthesis gas (mixed gas including carbon monoxide gas and hydrogen gas as main components).

Specifically, first, the above natural gas is supplied to the desulfurizing reactor 10 along with the hydrogen gas separated by the hydrogen separating apparatus 26. The desulfurizing reactor 10 hydrogenates and desulfurizes sulfur components included in the natural gas using the hydrogen gas, with a ZnO catalyst. By desulfurizing natural gas in advance in this way, it is possible to prevent a decrease in activity of a catalyst used in the reformer 12, the bubble column reactor 30, etc. because of sulfur.

The natural gas (may also contain carbon dioxide) desulfurized in this way is supplied to the reformer 12 after the carbon dioxide ($CO_2$) gas supplied from a carbon-dioxide supply source (not shown) is mixed with the steam generated in the waste heat boiler 14. The reformer 12 reforms natural gas by using carbon dioxide and steam to produce high-temperature synthesis gas including carbon monoxide gas and hydrogen gas as main components, by the above steam and carbon-dioxide-gas reforming method. At this time, the reformer 12 is supplied with, for example, fuel gas for a burner disposed in the reformer 12 and air, and reaction heat required for the above steam and $CO_2$ reforming reaction, which is an endothermic reaction, is provided by the heat of combustion of the fuel gas in the burner and radiant heat in a furnace of the reformer 12.

The high-temperature synthesis gas (for example, 900° C., 2.0 MPaG) produced in the reformer 12 in this way is supplied to the waste heat boiler 14, and is cooled down by the heat exchange with the water which circulates through the waste heat boiler 14 (for example, 400° C.), thereby exhausting and recovering heat. At this time, the water heated by the synthesis gas in the waste heat boiler 14 is supplied to the gas-liquid separator 16. From this gas-liquid separator 16, a gas component is supplied to the reformer 12 or other external devices as high-pressure steam (for example, 3.4 to 10.0 MPaG), and water as a liquid component is returned to the waste heat boiler 14.

Meanwhile, the synthesis gas cooled down in the waste heat boiler 14 is supplied to the absorption column 22 of the $CO_2$ removal unit 20, or the bubble column reactor 30, after condensate is separated and removed from the gas-liquid separator 18. The absorption column 22 absorbs carbon dioxide gas included in the synthesis gas into the absorbent, to separate the carbon dioxide gas from the synthesis gas. The absorbent including the carbon dioxide gas within this absorption column 22 is introduced into the regeneration column 24, the absorbent including the carbon dioxide gas is heated and subjected to stripping treatment with, for example, steam, and the resulting desorbed carbon dioxide gas is recycled to the reformer 12 from the regeneration column 24, and is reused for the above reforming reaction.

The synthesis gas produced in the synthesis gas production unit 3 in this way is supplied to the bubble column reactor 30 of the above FT synthesis unit 5. At this time, the composition ratio of the synthesis gas supplied to the bubble column reactor 30 is adjusted to a composition ratio (for example, $H_2:CO=2:1$ (molar ratio)) suitable for the FT synthesis reaction. In addition, the pressure of the synthesis gas supplied to the bubble column reactor 30 is raised to be pressure (for example, 3.6 MPaG) suitable for the FT synthesis reaction by a compressor (not shown) provided in a pipe which connects the $CO_2$ removal unit 20 with the bubble column reactor 30. Note that, the compressor may be removed from the pipe.

Further, a portion of the synthesis gas, the carbon dioxide gas of which has been separated by the above $CO_2$ removal unit 20, is also supplied to the hydrogen separating apparatus 26. The hydrogen separating apparatus 26 separates the hydrogen gas included in the synthesis gas, by the adsorption and desorption (hydrogen PSA) utilizing a pressure difference as described above. This separated hydrogen is continuously supplied from a gas holder (not shown), etc. via a compressor (not shown) to various hydrogen-utilizing reaction devices (for example, the desulfurizing reactor 10, the WAX fraction hydrocracking reactor 50, the kerosene and gas oil fraction hydrotreating reactor 52, the naphtha fraction hydrotreating reactor 54, etc.) which perform predetermined reactions utilizing hydrogen within the liquid fuel synthesizing system 1.

Next, the above FT synthesis unit 5 synthesizes liquid hydrocarbons by the FT synthesis reaction from the synthesis gas produced by the above synthesis gas production unit 3.

Specifically, the synthesis gas produced by the above synthesis gas production unit 3 flows into the reactor main body 80 of the bubble column reactor 30 from the bottom of the body 80, and flows up through the slurry 82 stored in the reactor main body 80. At this time, within the reactor main body 80, the carbon monoxide and hydrogen gas which are included in the synthesis gas react with each other by the FT synthesis reaction, thereby producing hydrocarbons. Moreover, by circulating water through the cooling pipe 86 at the time, of this synthesis reaction, the heat of the FT synthesis reaction is removed, and the water heated by this heat exchange is vaporized into steam. As for this water vapor, the water liquefied in the gas-liquid separator 34 is returned to the cooling pipe 86, and the gas component is supplied to an external device as medium-pressure steam (for example, 1.0 to 2.5 MPaG).

The liquid hydrocarbons 822 synthesized in the bubble column reactor 30 in this way are extracted as the slurry 82 from the bubble column reactor 30, and are introduced into the separator 36. The separator 36 separates the extracted slurry 82 into a solid component, such as the catalyst particles 824, and a liquid component including the liquid hydrocarbons 822. A portion of the separated solid component, such as the catalyst particles 824, is returned to the bubble column reactor 30, and a liquid component of the slurry is supplied to the first fractionator 40. From the unreacted gas outlet 806 of the bubble column reactor 30; unreacted synthesis gas, and a gas component of the synthesized hydrocarbons are introduced into the gas-liquid separator 38. The gas-liquid separator 38 cools down these gases to separate some condensed liquid hydrocarbons to introduce them into the first fractionator 40. Meanwhile, as for the gas component separated in the gas-liquid separator 38, unreacted synthesis gases (CO and $H_2$) are returned to the bottom of the bubble column reactor 30, and are reused for the FT synthesis reaction. Further, the flare gas other than target products, including as a main component hydrocarbon gas having a small carbon number (equal to or less than $C_4$), is introduced into an external combustion facility (not shown), is combusted therein, and is then emitted to the atmosphere.

Next, the first fractionator 40 heats the liquid hydrocarbons (whose carbon numbers are various) supplied via the separator 36 and the gas-liquid separator 38 from the bubble column reactor 30 as described above, to fractionally distill the liquid hydrocarbons using a difference in boiling point. Thereby, the first fractionator 40 separates and refines the liquid hydrocarbons into a naphtha fraction (whose boiling point is less than about 150° C.), a kerosene and gas oil fraction (whose boiling point is about 150 to 350° C.), and a WAX fraction (whose boiling point is greater than about 350° C.). The liquid hydrocarbons (mainly $C_{21}$ or more) as the WAX fraction extracted from the bottom of the first fractionator 40 are transferred to the WAX fraction hydrocracking reactor 50, the liquid hydrocarbons (mainly $C_{11}$ to $C_{20}$) as the kerosene and gas oil fraction extracted from the middle portion of the first fractionator 40 are transferred to the kerosene and gas oil fraction hydrotreating reactor 52, and the liquid hydrocarbons (mainly $C_5$ to $C_{10}$) as the naphtha fraction extracted from the upper portion of the first fractionator 40 are transferred to the naphtha fraction hydrotreating reactor 54.

The WAX fraction hydrocracking reactor 50 hydrocracks the liquid hydrocarbons as the WAX fraction with a large carbon number (approximately $C_{21}$ or more), which has been supplied from the lower portion of the first fractionator 40, by using the hydrogen gas supplied from the above hydrogen separating apparatus 26, to reduce the carbon number to $C_{20}$ or less. In this hydrocracking reaction, hydrocarbons with a small carbon number and with low molecular weight are generated by cleaving C—C bonds of hydrocarbons with a large carbon number, using a catalyst and heat. A product including the liquid hydrocarbons hydrocracked by this WAX fraction hydrocracking reactor 50 is separated into gas and liquid in the gas-liquid separator 56, the liquid hydrocarbons of which are transferred to the second fractionator 70, and the gas component (including hydrogen gas) of which is transferred to the kerosene and gas oil fraction hydrotreating reactor 52 and the naphtha fraction hydrotreating reactor 54.

The kerosene and gas oil fraction hydrotreating reactor 52 hydrotreats liquid hydrocarbons (approximately $C_{11}$ to $C_{20}$) as the kerosene and gas oil fractions having an approximately middle carbon number, which have been supplied from the central portion of the first fractionator 40, by using the hydrogen gas supplied via the WAX fraction hydrocracking reactor 50 from the hydrogen separating apparatus 26. This hydrotreating reaction is an isomerization and a reaction which adds hydrogen to unsaturated bonds of the above liquid hydrocarbons, to saturate the liquid hydrocarbons and to mainly generate side-chain saturated hydrocarbons. As a result, a product including the hydrotreated liquid hydrocarbons is separated into gas and liquid in the gas-liquid separator 58, the liquid hydrocarbons are transferred to the second fractionator 70, and the gas component (including hydrogen gas) is reused for the above hydrogenation reaction.

The naphtha fraction hydrotreating reactor 54 hydrotreats liquid hydrocarbons (approximately $C_{10}$ or less) as the naphtha fraction with a low carbon number, which have been supplied from the upper portion of the first fractionator 40, by using the hydrogen gas supplied via the WAX fraction hydrocracking reactor 50 from the hydrogen separating apparatus 26. As a result, a product including the hydrotreated liquid hydrocarbons is separated into gas and liquid in the gas-liquid separator 60, the liquid hydrocarbons are transferred to the naphtha stabilizer 72, and the gas component (including hydrogen gas) is reused for the above hydrogenation reaction.

Next, the second fractionator 70 distills the liquid hydrocarbons supplied from the WAX fraction hydrocracking reactor 50 and the kerosene and gas oil fraction hydrotreating reactor 52 as described above. Thereby, the second fractionator 70 separates and refines the liquid hydrocarbons into hydrocarbons (whose boiling point is less than about 150° C.) with a carbon number of 10 or less, kerosene (whose boiling point is about 150 to 250° C.), gas oil (whose boiling point is about 250 to 350° C.), and remaining WAX fraction (whose boiling point is higher than 350° C.) from the WAX fraction hydrocracking reactor 50. The gas oil is extracted from a lower portion of the second fractionator 70, and the kerosene is extracted from a middle portion thereof. Meanwhile, a hydrocarbon gas with a carbon number of 10 or less is extracted from the top of the second fractionator 70, and is supplied to the naphtha stabilizer 72.

Moreover, the naphtha stabilizer 72 distills the hydrocarbons with a carbon number of $C_{10}$ or less, which have been supplied from the above naphtha fraction hydrotreating reactor 54 and second fractionator 70. Thereby, the naphtha stabilizer 72 separates and refines naphtha ($C_5$ to $C_{10}$) as a product. Accordingly, high-purity naphtha is extracted from a lower portion of the naphtha stabilizer 72. Meanwhile, the flare gas other than target products, which contains as a main component hydrocarbons with a carbon number lower than or equal to a predetermined number (lower than or equal to $C_4$), is discharged from the top of the naphtha stabilizer 72. Further, the flare gas is introduced into an external combustion facility (not shown), is combusted therein, and is then discharged to the atmosphere.

The process (GTL process) of the liquid fuel synthesizing system 1 has been described hitherto. Subsequently, the procedure of extracting contents using the extracting device 42 from the bubble column reactor 30 will be described in detail with reference to FIG. 2.

At the beginning, all the two-way valves V1 to V7 are closed, and the three-way valve 49 is opened toward the storage tank 44. Thus, during operation of the bubble column reactor 30, when the two-way valves V2 and V3 are opened and the two-way valve V1 is then opened gradually, the contents in which the slurry and the source gas are mixed flow into the storage tank 44 through the main pipe 45. If the internal space of the main pipe 45 is filled with the contents, the two-way valve V1 is closed, and the three-way valve 49 is switched to the extraction vessel 43. At this time, the two-way valve V7 is maintained in a closed state. Subsequently, the two-way valve V6 is opened slightly, and unnecessary gas included in the contents is discharged out of the system through the gas vent pipe 47 from the main pipe 45. Thereby, unnecessary gas, such as an inflammable gas or a toxic gas included in the contents can be safely removed from the contents held in the main pipe 45.

After the two-way valves V2 and V3 are closed, and subsequently the two-way valves V4 and V7 are opened, the two-way valve V5 is opened gradually, thereby pressurizing and supplying an inert gas (for example, nitrogen gas or argon gas), which does not include oxygen, to the main pipe 45 through the inert gas supply pipe 46B from the inert gas supply source 46A. When the inert gas is supplied to the main pipe 45, the contents in the main pipe 45 is replaced with the inert gas, and the contents are extracted from the main pipe 45 through the extraction pipe 48 to the extraction vessel 43. At this time, the two-way valve V6 may be closed or may be opened. The contents including a predetermined quantity of contents obtained by the quantitative section 90 and filled into the main pipe 45 from the two-way valve V1 to the three-way valve 49 and contents filled in the extraction pipe 48 are discharged to the extraction vessel 43. In particular, in the quantitative section 90 which is installed inclinedly, the contents obtained by the quantitative section 90 are smoothly discharged from the quantitative section 90 by the action of gravity on itself. Moreover, the gas which has remained in the contents is vented upward smoothly along the upper face of the quantitative section 90 formed in a planar shape. Accordingly, the contents obtained by the quantitative section 90 are discharged to the extraction vessel 43, without including unnecessary gas. If the contents have been discharged to the extraction vessel 43, the two-way valves V4, V5, and V7 are closed, thereby completing a series of extraction.

According to the liquid fuel synthesizing system 1 configured as described above, the contents can be safely discharged from the bubble column reactor 30 kept at high temperature and high pressure. Further, since the contents obtained by the quantitative section 90 are extracted to the extraction vessel 43, a required quantity of contents can be accurately extracted a number of times. That is, it is possible to carry out sampling having a constant quantity of extraction and high repeatability.

Although contents may be blown off suddenly to the extraction vessel 43, only liquid contents are discharged to the extraction vessel 43 after unnecessary gas is removed. Therefore, such sudden blow-off can be prevented and the extraction operation can be performed safely.

Figure 5:
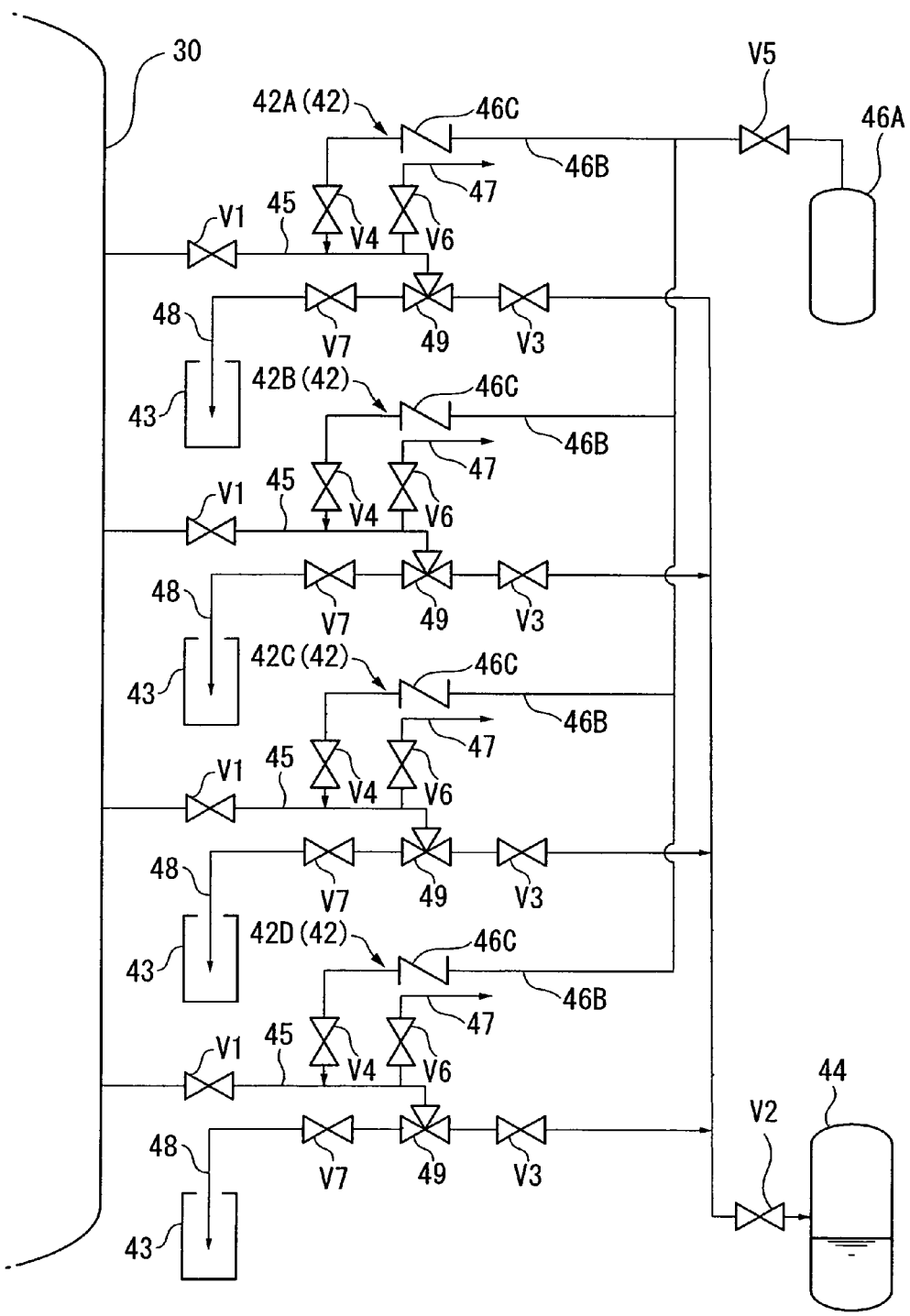
FIG. 5 is a schematic diagram showing an extracting device constituting a liquid fuel synthesizing system according to a second embodiment of the present invention.

Next, a second embodiment of the present invention will be described with reference to FIG. 5. In addition, the constituent components already described in the above first embodiment will be denoted by the same reference numerals, and the detailed description thereof will be omitted.

The bubble column reactor 30 of the present embodiment is provided with a plurality of extracting devices 42. A plurality of extracting devices 42A to 42D is installed in the bubble column reactor 30 so as to be spaced apart at equal intervals in the vertical direction of this reactor. The structures of the extracting devices 42A to 42D are the same as those described in the above first embodiment. However, since there is only one storage tank 44, the main pipes 45 of the respective extracting devices 42A to 42D are merged into one on the side of the storage tank 44, and this merged portion is provided with one two-way valve V2 shared by the respective extracting devices 42A to 42D. Further, since there is only one inert gas supply source 46A, the inert gas supply pipes 46B of the respective extracting devices 42A to 42D are merged into one on the side of the inert gas supply source 46A, and this merged portion is provided with one two-way valve V5 shared by the respective extracting devices 42A to 42D. In addition, in FIG. 5, the quantitative sections 90 provided in the respective extracting devices 42A to 42D are omitted.

Subsequently, the procedure of extracting the contents using the extracting devices 42A to 42D from the bubble column reactor 30 will be described in detail.

At the beginning, in each of the extracting devices 42A to 42D, all the two-way valves V1 to V7 are closed, and the three-way valve 49 is opened toward the storage tank 44.

Thus, during operation of the bubble column reactor 30, in each of the extracting devices 42A to 42D, when the two-way valves V2 and V3 are opened and the two-way valve. V1 is then opened gradually, the contents in which the slurry and the source gas are mixed flow into the storage tank 44 through the main pipe 45. In each of the extracting devices 42A to 42D, if the internal space of the main pipe 45 is filled with the contents, the two-way valve V1 is closed, and the three-way valve 49 is switched to the extraction vessel 43. At this time, the two-way valve V7 is maintained in a closed state. Subsequently, in each of the extracting devices 42A to 42D, the two-way valve V6 is opened slightly, and unnecessary gas included in the contents is discharged out of the system through the gas vent pipe 47 from the main pipe 45.

In each of the extracting devices 42A to 42D, after the two-way valves V2 and V3 are closed, and subsequently the two-way valves V4 and V7 are opened, the two-way valve V5 is opened gradually, thereby pressurizing and supplying an inert gas (for example, nitrogen gas or argon gas), which does not include oxygen, to the main pipe 45 through the inert gas supply pipe 46B from the inert gas supply source 46A. In each of the extracting devices 42A to 42D, when the inert gas is supplied to the main pipe 45, the contents in the main pipe 45 are replaced with the inert gas, and the contents are extracted from the main pipe 45 through the extraction pipe 48 to the extraction vessel 43. At this time, the two-way valve V6 may be closed or may be opened. The contents including a predetermined quantity obtained by the quantitative section 90 and filled into the main pipe 45 from the two-way valve V1 to the three-way valve 49 and the extraction pipe 48 are discharged to the extraction vessel 43 of each of the extracting devices 42A to 42D. If the contents have been discharged to the extraction vessel 43, the two-way valves V4, V5, and V7 are closed, thereby completing a series of extraction.

According to the liquid fuel synthesizing system configured as described above, the plurality of extracting devices 42A to 42D are installed so as to be spaced apart at equal intervals in the vertical direction of the bubble column reactor 30. Thus, it is possible to investigate the carbon number distribution of a product (i.e., a hydrocarbon compound) included in contents in the vertical direction within the reactor 30, the distribution of reaction state of slurry and a synthesis gas in the vertical direction within the synthesis reactor, and the concentration distribution of the slurry in the vertical direction within the synthesis reactor.

In the above second embodiment, the plurality of extracting devices 42A to 42D are installed so as to be spaced apart in the vertical direction of the bubble column reactor 30. However, the plurality of extracting devices 42A to 42D may be installed so as to be spaced apart in the peripheral direction of the bubble column reactor 30. Thereby, it is possible to investigate the carbon number distribution of a product (i.e., a hydrocarbon compound) included in contents in the peripheral direction within the reactor 30, the distribution of reaction state of slurry and a synthesis gas in the peripheral direction within the synthesis reactor, and the concentration distribution of the slurry in the peripheral direction within the synthesis reactor.

In the above first and second embodiments, the extraction vessel 43 may be put into a case for preventing scattering of contents, and the contents may be discharged toward the extraction vessel 43 from the extraction pipe 48 within the case. Further, the inclination angle θ of the quantitative section 90 to the horizontal plane may be suitably changed according to the angle of repose which depends on the property of contents.

In the above embodiments, natural gas is used as a hydrocarbon raw material to be supplied to the liquid fuel synthesizing system 1. However, for example, other hydrocarbon raw materials, such as asphalt and residual oil, may be used. Further, although the liquid fuel synthesizing system 1 has been described in the above embodiments, the present invention can be applied to a synthesis reaction system of a hydrocarbon compound which synthesizes a hydrocarbon compound by a chemical reaction of a synthesis gas including at least hydrogen and carbon monoxide as main components, and slurry.

While preferred embodiments of the invention have been described and illustrated above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

INDUSTRIAL APPLICABILITY

The present invention relates to a method of extracting contents from the inside of a reactor kept at high temperature and high pressure. The method includes the steps of introducing the contents of the reactor into a pipe having an internal space which communicates with the reactor, closing the pipe to enclose the contents in the internal space, removing unnecessary gas from the internal space, and supplying an inert gas to the internal space, thereby replacing the contents enclosed in the internal space with the inert gas. The contents are discharged from the internal space by replacing the contents enclosed in the internal space with the inert gas.

According to the present invention, contents in which a slurry and a synthesis gas are mixed can be safely and accurately extracted from the synthesis reactor.

The invention claimed is:

1. A method of extracting contents from the inside of a reactor kept at high temperature and high pressure, the method comprising the steps of:
   introducing the contents of the reactor which includes unnecessary gas into a pipe having an internal space which communicates with the reactor;
   closing the pipe to enclose the contents including the unnecessary gas in the internal space;
   removing the unnecessary gas from the internal space; and
   replacing the contents from which the unnecessary gas is removed with an inert gas by supplying the inert gas to the internal space, and
   discharging the contents from the internal space by replacing the contents enclosed in the internal space with the inert gas.

2. The method of extracting contents according to claim 1, wherein the reactor is a synthesis reactor which synthesizes a hydrocarbon compound by a chemical reaction between a synthesis gas including hydrogen and carbon monoxide as main components and a slurry having solid catalyst particles suspended in liquid.

3. A synthesis reaction system of a hydrocarbon compound comprising:
   a synthesis reactor which synthesizes a hydrocarbon compound by a chemical reaction between a synthesis gas including hydrogen and carbon monoxide as main components and a slurry having solid catalyst particles suspended in liquid;
   an extracting device which extracts contents, in which the synthesis gas and the slurry are mixed, from the synthesis reactor; and
   a storage tank which stores the remnants of the contents extracted from the synthesis reactor, wherein
   the extracting device includes:
   a main pipe interposed between the synthesis reactor and the storage tank, having an internal space communicating with the synthesis reactor, and allowing the contents including unnecessary gas introduced from the synthesis reactor to be enclosed in the internal space;
   an inert gas supply section supplying an inert gas to the internal space;
   a gas vent pipe allowing the unnecessary gas to be removed from the internal space of the main pipe on the downstream side of a connection point with the inert gas supply section;
   an extraction pipe allowing the contents from which the unnecessary gas is removed with an inert gas to be discharged to an extraction vessel through the main pipe on the downstream side of a connection point with the gas vent pipe; and
   a three-way valve provided at a connection point between the main pipe and the extraction pipe to switch a discharge direction of the contents enclosed in the internal space to either the storage tank or the extraction vessel.

4. The synthesis reaction system of a hydrocarbon compound according to claim 3, wherein a plurality of the extracting devices are installed in the synthesis reactor so as to be spaced apart in a vertical direction of the reactor.

5. The synthesis reaction system of a hydrocarbon compound according to claim 3, wherein a plurality of the extracting devices are installed in the synthesis reactor so as to be spaced apart in a peripheral direction of the reactor.

6. The synthesis reaction system of a hydrocarbon compound according to any one of claims 3 to 5, wherein the main pipe is provided with a quantitative section which obtains a predetermined quantity of the contents.

7. The synthesis reaction system of a hydrocarbon compound according to claim 6, wherein the quantitative section is formed in the shape of a pipe of which the capacity of the internal space is almost equal to the predetermined quantity, and is installed so as to incline at a predetermined angle to a horizontal plane.

8. The synthesis reaction system of a hydrocarbon compound according to claim 7, wherein the size of the predetermined angle is equal to or more than the angle of repose of the catalyst particles.

9. The synthesis reaction system of a hydrocarbon compound according to claim 7, wherein an upper face of the quantitative section is formed in a planar shape.

* * * * *

UNITED STATES PATENT AND TRADEMARK OFFICE
CERTIFICATE OF CORRECTION

PATENT NO.        : 8,398,340 B2                              Page 1 of 1
APPLICATION NO. : 12/736114
DATED             : March 19, 2013
INVENTOR(S)       : Onishi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 371 days.

Signed and Sealed this

First Day of September, 2015

Michelle K. Lee
*Director of the United States Patent and Trademark Office*